United States Patent [19]

Raulerson

[11] Patent Number: 4,813,938
[45] Date of Patent: Mar. 21, 1989

[54] CATHETER INTRODUCTION SYRINGE

[76] Inventor: J. Daniel Raulerson, 1203 Belleville Ave., Brewton, Ala. 36426

[21] Appl. No.: 97,758

[22] Filed: Sep. 17, 1987

[51] Int. Cl.[4] ............................................. A61M 5/00
[52] U.S. Cl. ................... 604/167; 604/236; 604/156; 604/169
[58] Field of Search ................. 251/149.1, 149.3, 149; 604/167, 169, 156, 159, 124, 125, 236; 137/223

[56] References Cited

U.S. PATENT DOCUMENTS 4,274,408  6/1981  Nimrod ............................ 604/52 X

FOREIGN PATENT DOCUMENTS 2415196 10/1975 Fed. Rep. of Germany ...... 604/159
2507119  9/1976 Fed. Rep. of Germany ...... 604/159
3042229  5/1982 Fed. Rep. of Germany ...... 604/167

Primary Examiner—Samuel Scott
Assistant Examiner—Carl D. Price
Attorney, Agent, or Firm—A. W. Fisher, III

[57] ABSTRACT

A catheter introduction syringe for the introduction of a catheter or catheter guide wire into a patient's body, the catheter introduction syringe comprises a hollow substantially cylindrical syringe barrel to support a needle thereon having a substantially cylindrical plunger slidably disposed therein, the substantially cylindrical plunger includes a centrally disposed channel formed longitudinally therethrough having a valve assembly disposed in operative relationship relative to the centrally disposed channel to prevent passage of air or liquid therethrough during flushing or aspirating of the catheter introduction syringe and permit the introduction of a catheter or catheter guide wire through the centrally disposed channel, hollow substantially cylindrical syringe barrel and needle for introduction into the patient's body without the flow of air or liquid through the centrally disposed channel.

20 Claims, 1 Drawing Sheet

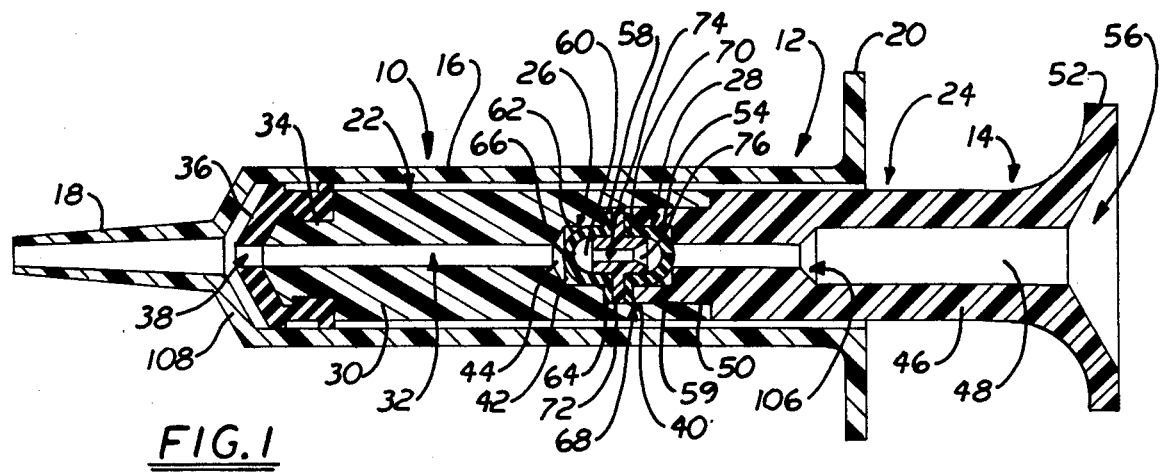

CATHETER INTRODUCTION SYRINGE

BACKGROUND OF THE INVENTION

1. Field of the Invention

A catheter introduction syringe comprising a barrel and plunger combination wherein the plunger includes a centrally disposed passage having a valve assembly disposed therein to prevent the flow of fluid therethrough and permit the introduction of a catheter.

2. Description of the Prior Art

The art of introducing a catheter into a patient's body is difficult and often dangerous.

Commonly the central venous catheter placement is performed in the following manner:

(1) The patient is placed in Trendelenburg position to distend the thoracic veins if the internal jugular or subclavian veins are to be cannulated. The patient is placed in a flat supine position for cannulation of the femoral veins.

(2) Using body landmarks, identified visually or by palpation, the vein is indentified by aspiration of blood. This is accomplished by gently aspirating a syringe as the needle is advanced. Once blood appears in the syringe presence of the needle within the lumen of the vein is confirmed.

(3) In cannulation, catheter-over-needle catheter is advanced off the needle and down (or up) the vein, or; the syringe is removed from the needle and a catheter is threaded through the needle and into the vein, or; the syringe is removed from the needle and a guidewire is threaded through the needle and into the vein lumen. The needle is then removed leaving the catheter or guidewire in place. If the guidewire is used a catheter is threaded over the guidewire and down the lumen of the vein and the guidewire is removed.

In deep vein cannulation, the deep veins of the chest are exposed to the pressures created by respiration. During the inspiratory phase of respiration negative pressure is transmitted to the veins. In expiration positive pressure is transmitted to the veins. Therefore, if a subclavian or internal jugular vein is exposed to atmospheric pressure blood will pass from the vein during expiration while air will be pulled into the vein during inspiration. It is this latter situation which creates a potentially dangerous condition. If enough air enters the vein and goes to the heart it can result in an air embolus to the brain with the development of a stroke.

Numerous devices have been developed and used for catheter introduction.

For example, U.S. Pat. 4,274,408 discloses a syringe-type device for inserting a catheter guide wire into a blood vessel including a syringe in which the plunger has a central passage extending through it. A thin feeder tube including a central passge is slidably disposed in the central passage of the plunger. The plunger passage is normally blocked by a sphere received in a seat provided by a rubber tip on inner edge of the plunger body. The needle is inserted into the blood vessel and the plunger is then partially withdrawn to permit blood to be observed in the body of the syringe for verification of proper needle positioning. The thin feeder tube is then slid through the central passage past the sphere to eject the sphere to open the plunger passage. The thin feeder tube is further advanced to bring the inner end into contact with the end wall of the syringe. In this position, the central passage of the thin feeder tube is aligned and in communication with the needle lumen. A catheter guide wire may then be fed into the blood vessel by sliding it through the central passage of the thin feeder tube and the needle lumen. The device is then removed from the guide wire, and a beveled catheter is inserted over the guide wire in the usual manner.

U.S. Pat. Nos. 4,233,982; 4,245,635 and 4,261,357 also show catheter assemblies for intravenous use including a ball or spherical element to selectively operate as a vale sealing means.

U.S. Pat. No. 4,483,340 discloses a dilation catheter including a balloon element configured to be retracted by axial twisting following deflation.

U.S. Pat. No. 4,314,555 shows an intravascular catheter comprising a flexible catheter tube having the proximal end affixed to the distal end of a tubular hub of a catheter. A seal cap is connected to the catheter hub with a flexible tube disposed between the seal cap and catheter hub. The inner wall thereof closely abuts against the outer wall of a cannula which guides the catheter through the blood vessel. A location bar is fixed to a hub of the cannula and protrudes toward the distal end of the catheter. A stopper is mounted on the catheter hub to engage the distal end of the location bar.

U.S. Pat. No. 4,601,706 shows a central venous pressure catheter having a long flexible tube containing at least three channels or lumens. At the tip end of the catheter a balloon surrounds the tube and is inflatable via one of the channels. A distal port and a proximal port in the wall of the tube are located on either side of the balloon, and are connected to the other two channels respectively. The tip end of the catheter may be inserted through a jugular vein into a patient's superior cava vein near the heart. The balloon is inflated to partially obstruct the flow of blood and to increase the blood pressure at a site of surgery at the head or neck of a patient in the upright position to avoid air embolism as well as to prevent bleeding.

U.S. Pat. No. 3,215,141 discloses an apparatus for use in intravenous introduction of a fluid comprising an elongate hollow needle of uniform inner and outer diameter. One end of the needle is formed to provide a sharpened edge for making a vein puncture. A tubular needle holder is removably mounted upon the opposite end of the needle. A sleeve is fitted over the needle holder. A pliable sac is secured at one end to the outer surface of the sleeve and extends rearwardly therefrom. The opposite end of the sac is sealed. A flexible catheter is positioned within the sac with one end in the needle and extendable outwardly of thereof by manipulation through the sac. The uniform outer diameter of the the needle permits positioning flatly against a patient's body after withdrawal of the needle from the vein puncture and removal of the needle holder from the needle.

U.S. Pat. No. 4,517,979 shows a detachable balloon catheter comprising a sealing valve assembly having an elongated passageway extending therethrough. An inflatable balloon having a mouth portion is bonded to the periphery of the sealing valve assembly. A small diameter cannula having a distal end which extends through the passageway in the sealing valve assembly. The small diameter cannula includes a connector terminal on the proximal end which is adapted to be coupled to a source of fluid pressure. The sealing valve assembly includes a valve mechanism which permits the passage of the cannula through the passageway but prevents the flow of fluid through the passagewan when the cannula is removed.

U.S. Pat. No. 4,160,383 shows a unitary vent-valve assembly, useful in urological applications.

U.S. Pat. Nos. 2,936,756; 3,097,646; 3,308,820; 3,766,916; 3,853,127; 3,859,998; 4,029,104; 4,177,814; 4,200,096; 4,346,698; 4,424,833; 4,529,399; 4,606,347; 4,610,665 and France Patent No. 2,004,771 show various syringes or medical instruments employing elastomeric plugs or membranes as seals or valves in combination with syringes.

U.S. Pat. Nos. 3,739,778 and 3,851,647 disclose catheter introduction systems using removable plugs to selectively seal fluid or catheter channels.

U.S. Pat. Nos. 105,776; 2,711,734 and 4,356,823 disclose suction control in valve elements movable to selectively control the flow of fluid through a valve body.

U.S. Pat. Nos. 4,243,034 and 4,464,177 show clamping structures to seal or control the flow of fluid.

Additional examples of the prior art are shown in U.S. Pat. Nos. 3,040,743; 3,335,723; 3,920,013; 3,978,863; 4,448,195; 4,479,497 and Italy Patent No. 407,607.

SUMMARY OF THE INVENTION

The present invention relates a catheter introduction syringe for the introduction of a catheter or catheter wire into a patient's body comprising a hollow syringe barrel having a plunger slidably disposed therein. As described more fully hereinafter, the catheter introduction syringe is capable of functioning as a standard air tight syringe as well as a device to introduce a catheter with a minimum resistance to the guide wire or catheter permitting tactile feel during introduction of the guide wire or catheter into the patient's body.

The plunger comprises first and second plunger element and a valve recess cooperatively formed therebetween to operatively house a valve assembly.

The first plunger element includes a first centrally disposed channel formed therethrough and a first valve seat formed therethrough. The second plunger element includes a second centrally disposed channel formed therethrough and a second valve seat formed therein.

The first and second valve seats cooperatively form the valve recess to receive the valve assembly therein. The valve assembly comprises a first and second valve element cooperatively forming a valve chamber therebetween. A normally closed centrally disposed slit or aperture is formed in the center of each valve element.

In use the catheter introduction syringe is aspirated by the retraction of the plunger permitting fluid to pass into the interior of the syringe barrel. During this aspiration, air is prevented from entering the valve chamber by the second valve element. Once aspirated, the catheter introduction syringe may then be flushed. While flushing, the first valve element prevents liquid from passing through the first centrally disposed channel into the valve chamber. Thus the catheter introduction syringe functions as an ordinary syringe.

Then a catheter or guide wire may be passed through the catheter introduction syringe and into the bloood vessel or body. The catheter or guide wire passes through the centrally disposed slits or apertures formed within the valve elements which form a seal therewith to prevent either liquid or air from passing through the valve chamber during the introduction of the catheter or guide wire.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is a cross-section side view of the catheter introduction syringe.

FIG. 2 is a detailed cross-sectional side view of an alternate embodiment of the valve assembly.

FIG. 3 is a cross-sectional side view of an alternate embodiment of the catheter introduction syringe.

Similar reference characters refer to similar parts throughout the several views of the drawings.

DETAILED DESCRIPTION OF THE PREFERRED EMBODIMENT

As shown in FIG. 1 the present invention relates a catheter introduction syringe generally indicated as 10 for the introduction of a catheter or catheter wire into a patient's body comprising a hollow substantially cylindrical syringe barrel generally indicated as 12 having a substantially cylindrical plunger generally indicated as 14 slidably disposed therein. As described more fully hereinafter, the catheter introduction syringe 10 is capable of functioning as a standard air tight syringe as well as a device to introduce a catheter with minimum resistance to the guide wire or catheter permitting tactile feel during introduction of the guide wire or catheter into the patient's body.

The hollow substantially cylindrical syringe barrel 12 comprises a hollow substantially cylindrical body 16 having a hollow barrel tip 18 to receive a needle (not shown) and a finger grasping element 20 formed on opposite ends thereof.

The substantially cylindrical plunger 14 comprises first and second plunger elements generally indicated as 22 and 24 respectively and a valve recess generally indicated as 26 cooperatively formed therebetween to operatively house a valve assembly generally indicated as 28 therein.

The first plunger element 22 comprises a first substantially cylindrical body 30 having a first centrally disposed channel 32 formed therethrough. One end of the first substantially cylindrical body 30 includes a reduced portion 34 to receive a plunger seal 36 having a centrally disposed seal aperture 38 formed therein, while the opposite end thereof includes a countersunk recess 40 to receive a portion of the second plunger element 24. A first valve seat 42 having a conical alignment recess 44 is formed between the countersunk recess 40 and the first centrally disposed channel 32.

The second plunger element 24 comprises a second substantially cylindrical body 46 having a second centrally disposed channel 48 formed therethrough. The inner end of the second substantially cylindrical body 46 includes a reduced portion 50 to be received within the countersunk recess 40 of the first substantially cylindrical body 30, while the opposite end includes a thumb element or rest 52 having a conical alignment guide recess 56 formed therein. A second valve seat 54 is formed on the inner end of the reduced portion 50 of the second substantially cylindrical body 46.

The first and second valve seats 42 and 54 cooperatively form the valve recess 26 to receive the valve assembly 28 therein. The valve assembly 28 comprises first and second one-way valve elements generally indicated as 58 and 59 respectively to cooperatively form a valve chamber 60 therebetween. Valve elements 58 and 59 comprise a flexible resilient hollow substantially hemispheric member 62 having an annular flange 64 formed about the periphery thereof. A normally closed centrally disposed slit or aperture 66 is formed in the center of each flexible resilient hollow substantially hemispheric member 62. To limit movement or deflection of the first and second valve elements 58 and 59 and maintain the sealing integrity thereof, a rigid valve support element generally indicated as 68 is disposed within the valve chamber 60. The rigid valve support element 68 comprises a substantially cylindrical body 70 having an annular flange 72 formed about the mid-portion thereof. The annular flange 72 is disposed between the annular flanges 64. A centrally disposed channel 74 including a conical alignment recess 76 is formed through the substantially cylindrical body 70. The conical alignment guide recess 56, conical alignment recess 76 and conical alignment recess 44 cooperatively form a catheter alignment means.

In use the catheter introduction syringe 10 is aspirated by the retraction of the substantially cylindrical plunger 14 permitting fluid to pass into the interior of the substantially cylindrical syringe barrel 12 through the hollow barrel tip 18. During this aspiration air is prevented from entering the valve chamber 60 by the second valve element 59. Once aspirated, the catheter introduction syringe 10 may then be flushed. While flushing, the first valve element 58 prevents liquid from passing through the first centrally disposed channel 32 into the valve chamber 60. Thus the catheter introduction syringe 10 functions as an ordinary syringe.

Then a catheter or guide wire may be passed through the catheter introduction syringe 10 and into the blood vessel or body cavity using the catheter aligned means. The catheter or guide wire passes through the centrally disposed slots or apertures 66 formed in the first and second valve elements 58 and 59 which form a seal therewith to prevent either liquid or air from passing through the valve chamber 60 during the introduction of the catheter of guide wire.

An alternate embodiment of the valve assembly 28' is shown in FIG. 2. The first plunger element 22' comprises a first substantially cylindrical body 30' having a first centrally disposed channel 32' formed therethrough. One end thereof includes a countersunk recess 40' having a conical alignment recess 44' formed between the countersunk recess 40' and the first centrally disposed channel 32'. The second plunger element 24' comprises a second substantially cylindrical body 46' having a second centrally disposed channel 48' formed therethrough. The inner end of the second substantially cylindrical body 46' includes a countersunk recess 78'.

The countersunk recesses 40' and 78' cooperatively form the valve recess 26' to receive the valve assembly 28 therein. The valve assembly 28' comprises first and second one-way valve elements generally indicated as 58' and 59' respectively disposed within a first and second valve seat generally indicated as 80' and 82' respectively cooperating forming a valve chamber 60' therebetween.

First and second valve elements 58' and 59' comprise a flexible resilient hollow substantially hemispheric member 62' having an annular flange 64' formed about the periphery thereof. A normally closed centrally disposed slit or aperture 66' is formed in the center of each flexible resilient hollow substantially hemispheric member 62'. To limit movement or deflection of the first and second valve elements 58' and 59' and maintain the sealing integrity thereof, the first and second valve seats 80' and 82' are formed within a rigid valve support element generally indicated as 68' disposed within the valve recess 26'. The rigid valve support element 68' includes a centrally disposed channel 74' extending between the first and second valve seat 80' and 82'. A conical alignment recess 76' is formed within the rigid valve support element 68'. The conical alignment guide recess 56', conical alignment recess 76' and conical alignment recess 44' cooperatively form a catheter alignment means.

The alternate embodiment of the valve assembly 28' functions similarly to that of the first embodiment as described above.

FIG. 3 shows an alternate embodiment of the catheter introduction syringe 10".

The hollow substantially cylindrical syringe barrel 12" comprises a hollow substantially cylindrical body 16" having a hollow barrel tip 18" to receive a needle (not shown) and a finger grasping element 20" formed on opposite ends thereof. A barrel vent 84" is formed through the sidewall of the hollow substantially cylindrical body 16" preferably near the finger grasping element 20". The finger grasping element 20" further includes a syringe barrel sealing means comprising inner and outer sealing elements indicated as 85" and 87" respectively to form air tight seals between the substantially cylindrical plunger 14" and finger grasping element 20" and between the finger grasping element 20" and the hollow substantially cylindrical syringe barrel 12" respectively.

The substantially cylindrical plunger 14" comprises first and second plunger elements generally indicated as 22" and 24" respectively and a valve recess means to operatively house a valve assembly means.

The first plunger element 22" comprises a first substantially cylindrical body 30" having a first centrally disposed channel 32" formed therethrough. One end of the first substantially cylindrical body 30" includes a reduced portion 34" to receive a plunger seal 36" having a centrally disposed seal aperture 38" formed therein, while the opposite end thereof includes a countersunk recess 40" to receive a portion of the second plunger element 24". A first valve seat including a conical alignement recess 44 is formed in the first plunger element 22".

The second plunger element 24" comprises a second substantially cylindrical body 46" having a second centrally disposed channel 48" formed therethrough. The inner end of the second substantially cylindrical body 46" includes a reduced portion 50" to be received within the countersunk recess portion 40" of the first substantially cylindrical body 30" while the opposite end includes a thumb element or rest 52" having a conical alignment guide recess 56" formed therein. A second valve seat 88" is formed on the inner end of the reduced portion 50" of the second substantially cylindrical body 46". A plunger vent 90" is formed through the side wall of the second plunger element 24". A plunger vent seal 92" is slidably mounted on the second substantially cylindrical body 46" to selectively seal the plunger vent 90" as described more fully hereafter.

The first and second valve seats 86" and 88" cooperatively form the valve recess means to receive a portion of the valve assembly means therein. The valve assembly means comprises a first and second valve element generally indicated as 94" and 96" respectively to cooperatively form a valve chamber 60" therebetween. The first valve element 94" comprises a flexible resilient hollow substantially hemispheric member 62" having an annular flange 64" formed about the periphery thereof. A normally closed centrally disposed slit or aperture 66" is formed in the center of the flexible resilient hollow substantially hemispheric member 62". A substantially cylindrical skirt 98" is formed on the annular flange 64" to limit movement or deflection of the first valve element 94" and maintain the sealing integrity thereof by engaging the sidewall 100" of the first valve seat 86". The second valve element 96" comprises a flexible resilient hollow tube generally indicated as 102" extending between the second valve seat 88" and a coupling element 104" extending from the inner end of the thumb element or rest 52". The cross-sectional diameter of the mid-portion of the flexible resilient hollow tube 102" is reduced to form the normally closed centrally disposed slit or aperture 66". The conical alignment recess 56" tapered alignment guide 106" and conical alignment recess 44" cooperatively form a catheter alignment means.

In use, the substantially cylindrical plunger 14" is inserted into the substantially cylindrical syringe barrel 12" with the plunger vent seal 92" preferably against the finger grasping element 20" with the plunger vent 90" open. The substantially cylindrical plunger 14" is then fully retracted as barrel vent 84" is occluded. The positive pressure created inside the hollow substantially cylindrical syringe barrel 12" is transmitted into the interior of the second plunger element 24" through the plunger vent 90". The plunger vent 90" is then sealed by the plunger vent seal 92" and the positive pressure within the interior of the second plunger element 24" maintained when the second plunger element 24" is fully retracted. When the barrel vent 84" is opened to atmospheric pressure, the plunger vent seal 92" remains over the plunger vent 90" as the catheter introduction syringe 10" is aspirated or flushed. The positive pressure within the second plunger element 24" maintains the sealing integrity of the second valve element 96".

When the catheter introduction syringe 10" is aspirated fluid passes into the hollow substantially cylindrical barrel 12" through the hollow barrel tip 18". During this aspiration air is prevented from entering the valve chamber 60" by the second valve element 96". Once aspirated, the catheter introduction syringe 10" may then be flushed. While flushing, the first valve element 94" prevents liquid from passing through the first centrally disposed channel 32" into the valve chamber 60". Thus the catheter introduction syringe 10" functions as an ordinary syringe.

Then a guidewire or catheter can be passed through the catheter introduction syringe 10" and into a blood vessel or body cavity as previously described.

The catheter alignment means may further include a conical alignment recess 106" formed in the second centrally disposed channel 48" and a conically shaped inner end 108" of the hollow substantially cylindrical syringe barrel tip 18.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A catheter introduction syringe for the introduction of a catheter or catheter guide wire into a patient's body, said catheter introduction syringe comprises a hollow syringe barrel to support a needle thereon having a plunger slidably disposed therein, said plunger comprises a first and second plunger element including a first and second valve seat respectively to cooperatively form a valve recess to operatively house a valve assembly therein and a centrally disposed channel formed longitudinally therethrough including a first and second centrally disposed channels formed through said first and second plunger elements respectively, said first and second centrally disposed channels disposed on opposite sides of said valve assembly, said valve assembly comprises a first and second valve element each including a flexible resilient valve member having a normally closed centrally disposed slit formed therein disposed within said first and second valve seats respectively to cooperatively form a valve chamber therebetween and a rigid valve support element disposed within said valve chamber arranged to limit deflection of said first and second valve elements and to maintain the sealing integrity thereof, said valve assembly disposed in operative relationship relative to said centrally disposed channel to prevent passage of air or liquid therethrough during flushing or aspirating of said catheter introduction syringe and permit the introduction a catheter or catheter guide wire through centrally disposed channel, said hollow syringe barrel and needle for introduction into the patient's body without the flow of air or liquid through said centrally disposed channel.

2. The catheter introduction syringe of claim 1 wherein each said flexible resilient valve member comprise a hollow substantially hemispheric member.

3. The catheter introduction syringe of claim 1 wherein said rigid valve support element comprises a body having a centrally disposed channel formed therethrough.

4. The catheter introduction syringe of claim 3 wherein said first plunger element includes a conical alignment recess formed therein and said rigid valve support element includes a conical alignment recess formed adjacent said centrally disposed channel to cooperatively form a catheter alignment means.

5. The catheter introduction syringe of claim 4 wherein said catheter alignment means further includes a conical recess formed in said second centrally disposed channel.

6. The catheter introduction syringe of claim 5 wherein said catheter alignment means further includes a conically shaped outer end portion of said syringe barrel.

7. A catheter introduction syringe for the introduction of a catheter or catheter guide wire into a patient's body, said catheter introduction syringe comprises a hollow syringe barrel to support a needle thereon having a plunger slidably disposed therein, said plunger includes a centrally disposed channel formed longitudinally therethrough having a valve assembly including a first and second valve element disposed in operative relationship relative to said centrally disposed channel to prevent passage of air or liquid therethrough during flushing or aspirating of said catheter introduction syringe and permit the introduction of a catheter or catheter guide wire through said centrally disposed channel, said hollow syringe barrel and needle for introduction into the patient's body without the flow of air or liquid through said centrally disposed channel, said plunger comprises a first and second plunger element including a first and second valve seat respectively to receive said first and second valve element respectively to cooperatively form a valve chamber therebetween, said first valve element comprises a flexible resilient hollow substantially hemispheric member including a normally closed centrally disposed slit formed therein and a annular skirt spaced from and formed about the at least a portion of said first valve element and arranged to engage said first valve seat to limit deflection of said first valve element to maintain the sealing integrity thereof.

8. The catheter introduction syringe of claim 7 wherein said centrally disposed channel comprises a first and second centrally disposed channel formed through said first and second plunger elements respectively, said first and second centrally disposed channels are disposed on opposite sides of said valve assembly.

9. The catheter introduction syringe of claim 7 wherein said second valve element comprise a flexible resilient hollow tube forming a normally closed slit formed in the mid-portion thereof.

10. The catheter introduction syringe of claim 9 further including means to maintain the sealing integrity of said second valve element with said plunger.

11. The catheter introduction syringe of claim 10 wherein said syringe barrel and said plunger include a barrel vent and plunger vent respectively formed therethrough, and a plunger vent seal slidably mounted on said plunger to seal said plunger vent when said barrel vent is occluded and said plunger is retracted relative to said syringe barrel to creater a positive pressure within said second plunger element to maintain the sealing integrity of said second valve element.

12. The catheter introduction syringe of claim 9 wherein said first plunger element includes a conical alignment recess formed therein and said second centrally disposed channel includes a conical alignment to cooperatively form a catheter alignment means.

13. The catheter introduction syringe of claim 12 wherein said catheter alignment means further includes a conical recess formed in said second centrally disposed channel.

14. The catheter introduction syringe of claim 12 wherein said catheter alignment means further includes tapered alignment guide formed in said flexible resilient hollow tube adjacent said normally closed slit formed in said mid-portion thereof.

15. The catheter introduction syringe of claim 12 wherein said catheter alignment means further includes a conically shaped outer end portion of said syringe barrel.

16. A catheter introduction syringe for the introduction of a catheter or catheter guide wire into a patient's body, said catheter introduction syringe comprises a hollow syringe barrel to support a needle thereon having a plunger slidably disposed therein, said plunger comprises a first and second plunger element each including a countersunk recess to cooperatively form a valve recess to operatively house a valve assembly therein and a centrally disposed channel formed longitudinally therethrough including a first and second centrally disposed channels formed through said first and second plunger elements respectively, said first and second centrally disposed channels disposed on opposite sides of said valve assembly, said valve assembly comprises a rigid valve support element having a first and second valve seat formed on opposite ends of a centrally disposed channel formed therethrough to receive a first and second valve element respectively to cooperatively form a valve chamber therebetween, said first and second valve elements each comprises a flexible resilient valve member having a normally closed centrally disposed slit formed therein, said rigid valve support element disposed in surrounding relationship relative to said first and second valve elements to limit deflection of said first and second valve elements and to maintain the sealing integrity thereof, said valve assembly disposed in operative relationship relative to said centrally disposed channel to prevent passage of air or liquid therethrough during flushing or aspirating of said catheter introduction syringe and permit the introduction of a catheter or cathetr guide wire through said centrally disposed channel, said hollow syringe barrel and needle for introduction into the patient's body without the flow of air or liquid through said centrally disposed channel.

17. The catheter introduction syringe of claim 16 wherein each said flexible resilient valve member comprise a hollow substantially hemispheric member.

18. The catheter introduction syringe of claim 16 wherein said first plunger element includes a conical alignment recess formed therein and said rigid valve support elements includes a conical alignment recess formed adjacent said centrally disposed channel to cooperatively form a catheter alignment means.

19. The catheter introduction syringe of claim 18 wherein said catheter alignment means further includes a conical recess formed in said second centrally disposed channel.

20. The catheter introduction syringe of claim 19 wherein said catheter alignment means further includes a conically shaped outer end portion of said syringe barrel.

* * * * *